(12) United States Patent
Tanabe et al.

(10) Patent No.: US 10,441,234 B2
(45) Date of Patent: Oct. 15, 2019

(54) RADIATION-PHASE-CONTRAST IMAGING DEVICE

(71) Applicant: Shimadzu Corporation, Kyoto (JP)

(72) Inventors: Koichi Tanabe, Uji (JP); Shingo Furui, Nara (JP); Hiroyuki Kishihara, Kizugawa (JP); Kenji Kimura, Yamatokoriyama (JP); Taro Shirai, Kyoto (JP); Takahiro Doki, Kyotanabe (JP); Satoshi Sano, Uji (JP); Akira Horiba, Uji (JP)

(73) Assignee: Shimadzu Corporation, Nakagyo-ku, Kyoto-shi, Kyoto (JP)

( * ) Notice: Subject to any disclaimer, the term of this patent is extended or adjusted under 35 U.S.C. 154(b) by 240 days.

(21) Appl. No.: 15/623,813

(22) Filed: Jun. 15, 2017

(65) Prior Publication Data

US 2018/0364182 A1 Dec. 20, 2018

(51) Int. Cl.
| | | |
|---|---|---|
| G03H 5/00 | (2006.01) | |
| A61B 6/00 | (2006.01) | |
| G21K 1/06 | (2006.01) | |
| G01N 23/041 | (2018.01) | |
| G01N 23/087 | (2018.01) | |

(52) U.S. Cl.
CPC ............ *A61B 6/482* (2013.01); *A61B 6/4291* (2013.01); *A61B 6/481* (2013.01); *A61B 6/484* (2013.01); *G01N 23/041* (2018.02); *G01N 23/087* (2013.01); *G21K 1/06* (2013.01); *G01N 2223/206* (2013.01); *G01N 2223/3308* (2013.01); *G21K 2201/067* (2013.01)

(58) Field of Classification Search
CPC ............ G01N 23/04; G01N 2223/206; G01N 23/041; G21K 1/06; G21K 2201/067; A61B 6/484; A61B 6/4291; A61B 6/481; A61B 6/482
See application file for complete search history.

(56) References Cited

U.S. PATENT DOCUMENTS 5,812,629 A * 9/1998 Clauser ................. A61B 6/032
378/37
8,908,825 B2 * 12/2014 Ohara ................... A61B 6/484
378/145
9,719,947 B2 * 8/2017 Yun ................... G01N 23/20075
(Continued)

FOREIGN PATENT DOCUMENTS

JP 2007-203074 A 8/2007
WO WO 2009104560 A1 8/2009

OTHER PUBLICATIONS

Office Action dated Oct. 3, 2017 of corresponding Japanese Patent Application No. JP 2014-258714.

*Primary Examiner* — Kiho Kim
(74) *Attorney, Agent, or Firm* — Muir Patent Law, PLLC (57) ABSTRACT

An X-ray phase-contrast imaging device capable of easily performing imaging of an object using X-rays of plural energies is provided. The disclosed exemplary configuration includes an X-ray source of a dual energy output type, and an FPD having a high energy X-ray detection surface and a low energy X-ray detection surface so that two types of imaging, imaging by high energy X-ray and imaging by low energy X-ray, can be performed. By imaging so as to scan the object while changing the relative position of the imaging system and the object, two types of imaging can be completed at once.

20 Claims, 8 Drawing Sheets

(56) References Cited

U.S. PATENT DOCUMENTS

| | | | |
|---|---|---|---|
| 2007/0183560 A1 | 8/2007 | Popescu et al. | |
| 2010/0322380 A1* | 12/2010 | Baeumer | G21K 1/06 378/62 |
| 2012/0099702 A1* | 4/2012 | Engel | A61B 6/00 378/62 |
| 2012/0236992 A1* | 9/2012 | Engel | A61B 6/00 378/62 |
| 2012/0243658 A1* | 9/2012 | Geller | A61B 6/00 378/16 |
| 2015/0260663 A1* | 9/2015 | Yun | G01N 23/20075 378/36 |
| 2016/0172148 A1* | 6/2016 | Behling | G21K 1/02 378/36 |
| 2016/0270198 A1* | 9/2016 | Behling | G21K 1/02 |
| 2017/0156686 A1* | 6/2017 | Koehler | A61B 6/06 |
| 2017/0343486 A1* | 11/2017 | Tanabe | G01N 23/04 |

\* cited by examiner

RADIATION-PHASE-CONTRAST IMAGING DEVICE

TECHNICAL FILED

The present invention relates to a radiation phase-contrast imaging device capable of imaging an internal structure of an object utilizing phase-contrast of radiation transmitted through the object.

BACKGROUND TECHNIQUE

Conventionally, various devices have been conceived as a radiation imaging device for imaging an internal structure of an object by making radiation transmit through the object. A commonly-used radiation imaging device is configured to take a radiation projection image by irradiating radiation to an object to make the radiation transmit through the object. In such a projection image, shading appears depending on the ease of permeation of radiation, which represents the internal structure of the object.

With such a radiation imaging device, only an object having a property capable of absorbing radiation to some extent can be imaged. For example, soft biological tissues hardly absorb radiation. Even if it is attempted to image such a tissue with a general device, almost nothing will be reflected on the projection image. When attempting to image an internal structure of an object that does not absorb radiation as described above, there is a theoretical limit in a general radiation imaging device.

Under the circumstances, a radiation phase-contrast imaging device configured to image an internal structure of an object utilizing a phase-contrast of transmitted radiation has been proposed. Such a device is configured to image an internal structure of an object using Talbot interference.

Talbot interference will be described. From the radiation source 53 shown in FIG. 11, phase-aligned radiation is irradiated. When making the radiation transmit through a phase grating 55 which is in a streak form, the image of the phase grating 55 appears on the projection surface which is apart from the phase grating 55 by a predetermined distance (Talbot distance). This image is called self-image. The self-image occurs only at the position where the projection surface is separated from the phase grating 55 by the Talbot distance, and the self-image is not just a projection image of the phase grating 55. The self-image is configured by interference fringes caused by interference of light. The reason that the self-image of the phase grating 55 appears at the Talbot distance is that the phase of radiation generated from the radiation source 53 is aligned. When the phase of radiation is disturbed, the self-image appearing at the Talbot distance is also disturbed.

Figure 11:
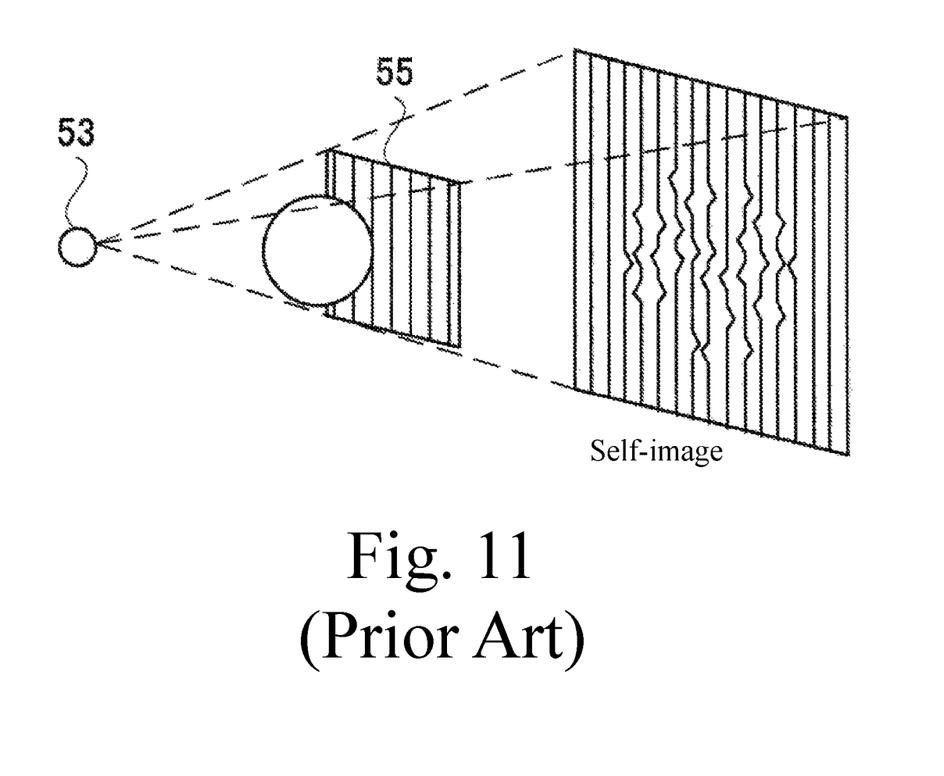
FIG. 11 is a schematic diagram illustrating a device of a conventional configuration.

The radiation phase-contrast imaging device is configured to image an internal structure of an object utilizing self-image disturbance. It is assumed that an object is placed between the radiation source and the phase grating 55. Since this object hardly absorbs radiation, most of the radiation incident on the object exits to the phase grating 55 side.

The radiation has not completely transmitted through the object as it is. The phase of the radiation changes when the radiation transmits through the object. The radiation exited the object transmits through the phase grating 55 with the phase changed. Observing the radiation on the projection plane arranged at the Talbot distance, a disturbance of the self-image of the phase grating 55 is recognized. The degree of disturbance of the phase grating 55 represents the radiation phase change.

The specific magnitude of the phase change of the radiation that transmitted through the object varies depending on where the radiation transmits through the object. If the object has a homogeneous structure, the change of the radiation phase remains the same no matter where the radiation transmits through the object. In general, however, an object has some internal structure. When making radiation transmit through such an object, the phase change does not remain the same. Therefore, when the phase change is known, the internal structure of the object can be known. The phase change can be known by observing the self-image of the phase grating 55 at the Talbot distance. The observation of the self-image may be carried out with a radiation detector placed at the Talbot distance (see, e.g., [9] International Patent Laid-Open Publication No. 2009104560, hereby incorporated by reference).

SUMMARY OF THE INVENTION

However, the conventional radiation phase-contrast imaging device has the following problems. That is, it is difficult for a conventional radiation phase-contrast imaging device to take a clear transparent image. This is because the energy of the radiation used for imaging cannot be optimized.

The energy of radiation emitted from the radiation source of the radiation phase-contrast imaging device cannot be anything. For example, if the energy of the radiation emitted by the radiation source is too low, the radiation will be absorbed in the object, making it difficult for the radiation to transmit through the object. Such low energy radiation is unsuitable for imaging. In order to grasp the internal structure of the object, it is necessary to observe the disturbance of the self-image caused by the transmission of the radiation through the object.

For example, if the energy of the radiation emitted from the radiation source is too high, the phase of the radiation becomes less likely to be affected by the object. Such high energy radiation is unsuitable for imaging. This is because that in order to grasp the internal structure of the object, it is necessary to observe the disturbance of the self-image caused by the transmission of the radiation through the object. In performing the radiation phase-contrast imaging as described above, there is a radiation energy suitable for imaging. The optimum energy for imaging varies depending on the object. In order to obtain a clear transparent image, in some cases, it is better to perform imaging again with a changed energy of the radiation.

Originally, in a conventional apparatus, the energy of radiation is set to one, and the configuration of the phase grating and the distance to the detection element are set in accordance with the set energy. Therefore, a conventional apparatus is not configured such that imaging is repeated while changing the energy of radiation.

However, from the principle of Talbot interference, even with a conventional device, it is not impossible to repeat imaging with different energies of radiation. In the conventional apparatus, however, such imaging is an extremely cumbersome work. Depending on the energy of radiation, the Talbot distance changes. Therefore, the distance from the phase grating 55 to the position where the self-image appears varies depending on the energy of radiation. To repeat imaging with different energy of radiation, it is required to re-adjust the distance between the phase grating 55 and the radiation detector each time the energy of radiation is changed.

The present invention has been made in view of such circumstances, and the object of the present invention is to provide a radiation phase-contrast imaging device capable of easily performing imaging of an object using radiation of a plurality of energies.

The radiation phase-contrast imaging device according to an embodiment of the present invention includes:

a radiation source configured to irradiate high energy radiation and low energy radiation;

a grating in which an absorber absorbing radiation and extending in one direction is arranged in a direction perpendicular to the one direction, the absorber generating Talbot interference when the radiation transmits therethrough;

a detection unit including a high energy radiation detection surface configured to detect a self-image of the grating related to the high energy radiation and a low energy radiation detection surface configured to detect a self-image of the grating related to the low energy radiation; and a position changing unit configured to change a relative position of an imaging system and an object so that a projection of the object moves on the detection surface while keeping a positional relationship of the radiation source, the grating, and the detection unit, the imaging system being configured by the radiation source, the grating, and the detection unit.

According to the present invention, it is possible to provide a radiation phase-contrast imaging device capable of easily performing imaging of an object using radiations of a plurality of energies. The configuration of some embodiments includes a radiation source of a dual energy output type and a detection unit equipped with a high energy radiation detection surface and a low energy radiation detection surface so that two types of imaging, i.e., imaging by high energy radiation and imaging by low energy radiation. By imaging so as to scan the object while changing the relative position of the imaging system and the object, two types of imaging can be completed simultaneously.

Further, in the above-described radiation phase-contrast imaging device, it is more preferable that a distance from the high energy radiation detection surface of the detection unit to the grating and a distance from the low energy radiation detection surface to the grating be different from each other.

The aforementioned configuration is a more specific exemplary implementation of the present invention. The Talbot distance, which indicates a distance from the grating as a starting point to a position where a self-image appears, varies according to the energy of radiation. By setting the distance from the high energy radiation detection surface to the grating and the distance from the low energy radiation detection surface to the grating independently, the distance from the detection surface to the grating can be assuredly set to the Talbot distance for the radiations of different energies.

Further, in the above-described radiation phase-contrast imaging device, it is more preferable that the position changing unit move the detection unit in a state in which a positional relationship of the high energy radiation detection surface and the low energy radiation detection surface is maintained.

The aforementioned configuration is a more specific exemplary implementation of the present invention. When the detection unit is moved while maintaining the positional relationship of the high energy radiation detection surface and the low energy radiation detection surface, scanning of the object can be performed with the distance from the detection surface to the grating assuredly held at the Talbot distance.

Further, in the above-described radiation phase-contrast imaging device, it is more preferable that the radiation phase-contrast imaging device further include a self-image generation unit configured to image a self-image from a detection result that the detection unit detects the radiation at the high energy radiation detection surface and a self-image from a detection result that the detection unit detects the radiation at the low energy radiation detection surface.

The aforementioned configuration is a more specific embodiment of the present invention. By individually performing imaging of a self-image for a high energy radiation and a self-image for a low energy radiation by the self-image generation unit, self-images can be generated assuredly for respective different radiation conditions.

Further, in the above-described radiation phase-contrast imaging device, it is more preferable that the radiation phase-contrast imaging device further include a transparent image generation unit configured to generate a transparent image of the object from the self-image related to the high energy radiation and imaged by the self-image generation unit and a transparent image of the object from the self-image related to the low energy radiation and imaged by the self-image generation unit.

The aforementioned configuration is a more specific embodiment of the present invention. By individually generating a transparent image for a high energy radiation and a transparent image for a low energy radiation by the transparent image generation unit, transparent images can be generated assuredly for respective different radiation conditions.

Accordingly, it is possible to provide a radiation phase-contrast imaging device capable of easily performing imaging of an object using radiations of a plurality of energies. A disclosed configuration includes a radiation source of a dual energy output type and a detection unit equipped with a high energy radiation detection surface and a low energy radiation detection surface so that two types of imaging, imaging by high energy radiation and imaging by low energy radiation. By imaging so as to scan the object while changing the relative position of the imaging system and the object, two types of imaging, can be completed at the same time, such as with a single scan of the object.

BRIEF DESCRIPTION OF THE DRAWINGS

Embodiments of the present invention are shown by way of example, and not limitation, in the accompanying drawings.

DETAILED DESCRIPTION

Next, embodiments for carrying out the invention will be described with reference to examples. The embodiments are described, and illustrated in the drawings, in terms of functional blocks or units. These blocks/units may be physically implemented by electronic (or optical) circuits such as logic circuits, discrete components, microprocessors, hard-wired circuits, memory elements, wiring connections, and the like, which may be formed together in a single integrated circuit (e.g., as a single semiconductor chip) or as separate integrated circuits and/or discrete components (e.g., several semiconductor chips wired together on a printed circuit board). These blocks/units may be implemented by a processor (e.g., a microprocessor, a controller, a CPU, a GPU) or processors that are programmed using software to perform various functions discussed herein. Each block/unit and/or module may be implemented by dedicated hardware, or as a combination of dedicated hardware to perform some functions and a processor to perform other functions. Also, each block/unit of the embodiments may be embodied by physically separate circuits and need not be formed as a single integrated circuit or a single processor. The X-ray in the embodiment corresponds to the "radiation" of the embodiment. The FPD in the embodiment is an abbreviation for a flat panel detector. The radiation phase-contrast imaging device of the present invention is suitable for fluoroscopy of a substrate for industrial use, fluoroscopy of a breast for medical use, etc., since imaging can be performed for an object M with little radiation absorption.

Figure 1:
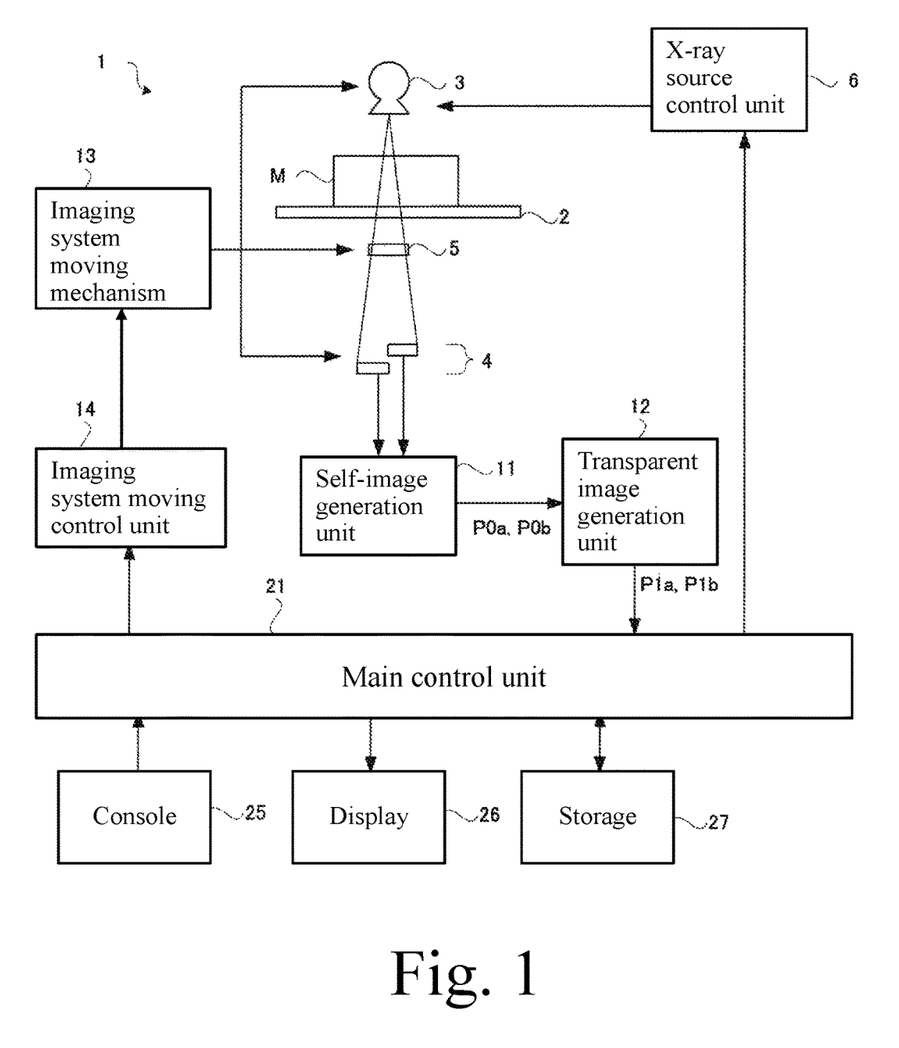
FIG. 1 is a functional block diagram describing an overall configuration of a device according to a first embodiment.

A radiation phase-contrast imaging device according to an embodiment of the present invention will be described. FIG. 1 shows an overall configuration of an imaging device 1 according to an embodiment of the present invention. As shown in FIG. 1, the imaging device 1 is provided with a platform 2 on which an object M is placed, an X-ray source 3 provided above the platform 2 and configured to irradiate an X-ray beam spreading in a pyramidal shape, and an FPD 4 configured to detect the X-ray generated from the X-ray source 3 and transmitted through the object M on the platform 2. A phase grating 5 for generating Talbot interference is provided at a position between the FPD 4 and the platform 2. Note that the X-ray source 3 corresponds to the "radiation source" of the embodiment, and the FPD 4 corresponds to the "detection unit" of the embodiment. Also note that the phase grating 5 corresponds to the "grating" of the embodiment.

The imaging device 1 is a radiation imaging device using Talbot interference. Therefore, the X-ray source 3 is configured to output an X-ray beam spreading in a phase-aligned radial pattern. Also, the distance between the phase grating 5 and the FPD 4 is set to the Talbot distance. With this setting, the self-image of the phase grating 5 will appear on the detection surface detecting the X-ray of the FPD 4. There are two detection surfaces in the present embodiment, and their functions are different. Details on this point will be described later.

The self-image generation unit 11 generates self-image images P0$a$ and P0$b$ in which the self-image of the phase grating 5 is reflected based on the output of the FPD 4. That is, the self-image generation unit 11 is configured to treat the detection data detected by the two detection surfaces of the FPD 4 as independent images and generate two types of self-image images P0$a$ and P0$b$. The generated self-image images P0$a$ and P0$b$ are output to the transparent image generation unit 12. Based on each of the self-image images P0$a$ and P0$b$ of the phase grating 5, the transparent image generation unit 12 generates transparent images P1$a$ and P1$b$ in which the phase-contrast of the X-ray generated in the object M is imaged.

Figure 2:
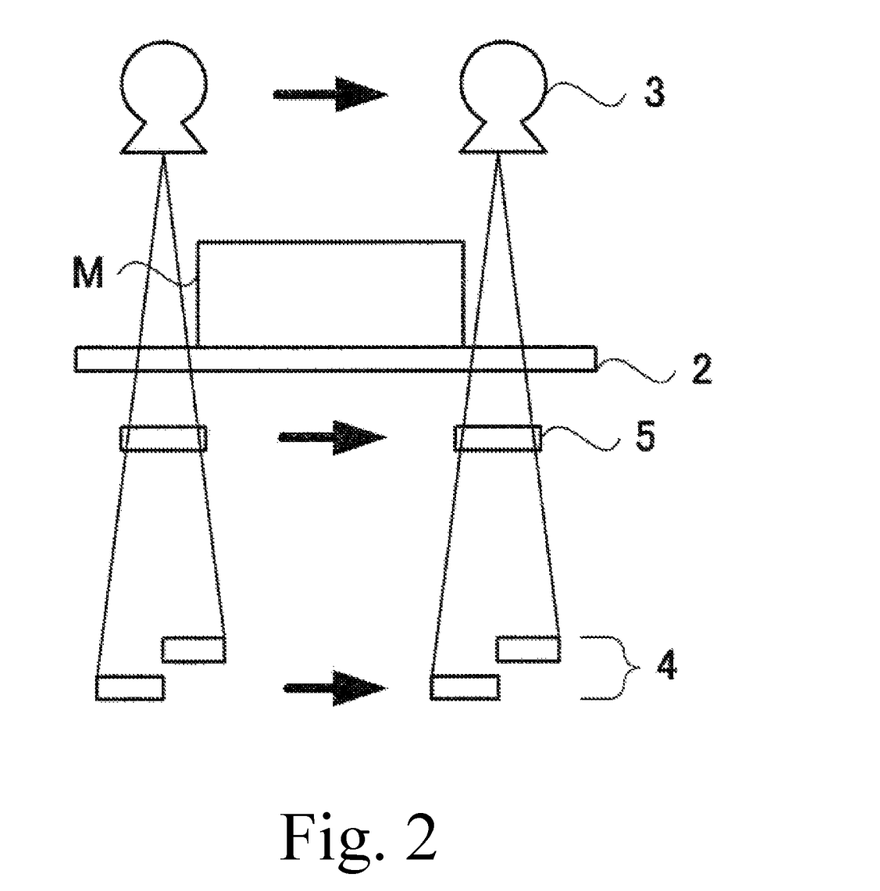
FIG. 2 is a schematic view illustrating the movement of the imaging system according to the first embodiment.

As shown in FIG. 2, the imaging system moving mechanism 13 (e.g. a servomotor) is configured such that the X-ray source 3, the FPD 4, and the phase grating 5 are moved with respect to the platform 2 while maintaining the positional relationship with each other. With the imaging system moving mechanism 13, the X-ray source 3, the FPD 4, and the phase grating 5 can be moved in a direction parallel to the platform 2. The imaging system moving mechanism 13 changes the relative position of the imaging system 3, 4, and 5 and the object M so that the projection of the object M moves linearly on the detection surface of the FPD 4 while maintaining the positional relationship of the X-ray source 3, the phase grating 5, and the FPD 4. The imaging system 3, 4, and 5 is composed of the X-ray source 3 configured to irradiate an X-ray, the phase grating 5 in which an absorption line 5$a$ absorbing radiation and extending in one direction is arranged in a direction perpendicular to the one direction, and the FPD 4 configured to detect the self-image of the phase grating 5 caused by the Talbot interference on the detection surface where detection elements configured to detect the radiation are arranged vertically and horizontally. The imaging system moving mechanism 13 moves the FPD 4 in a state in which the positional relationship of the high energy X-ray detection surface 4$b$ and the low energy X-ray detection surface 4$a$, which will be described later, is maintained. Note that the absorption line 5$a$ corresponds to the "absorber" of the embodiment and the imaging system moving mechanism 13 corresponds to the "position changing unit" of the embodiment.

In the case of the first embodiment, the change of the relative position of the object M with respect to the imaging system 3, 4, and 5 is executed by moving the imaging system 3, 4, 5 without moving the object M. The imaging system moving control unit 14 is provided for the purpose of controlling the imaging system moving mechanism 13.

The X-ray source control unit 6 is provided for the purpose of controlling the X-ray source 3. During the imaging, the X-ray source control unit 6 controls the X-ray source 3 so as to repeatedly output an X-ray beam in a pulsed manner. Every time the X-ray source 3 outputs the X-ray beam, the FPD 4 detects the X-ray that transmitted through the object M on the platform 2 and the phase grating 5 and sends the detection data to the self-image generation unit 11. As described above, the apparatus of the embodiment is configured to generate a self-image by repeatedly performing the X-ray imaging.

The continuous X-ray imaging is realized by the cooperation of the X-ray source control unit 6 and the imaging system moving control unit 14. That is, by the cooperation of both the control units, the operation of moving the imaging system 3, 4, and 5 above the high energy X-ray detection surface 4$a$ by the distance corresponding to the width of the high energy X-ray detection surface 4$a$ in the lateral direction (the later described width in the longitudinal direction in FIG. 4, or the moving direction), and the operation of irradiating the X-ray beam are repeated. Therefore, as the repeated imaging is continued, the position on the FPD 4 on which the object M is reflected moves by the width in the lateral direction of the high energy X-ray detection surface 4$a$. As described above, the X-ray source control unit 6 according to the first embodiment makes the X-ray source 3 irradiate the radiation every time the projection of the object M is moved on the detection surface by the width in the lateral direction of the high energy X-ray detection surface 4a. The width of the high energy X-ray detection surface 4a in the lateral direction coincides with the width of the low energy X-ray detection surface 4b in the lateral direction.

Figure 3:
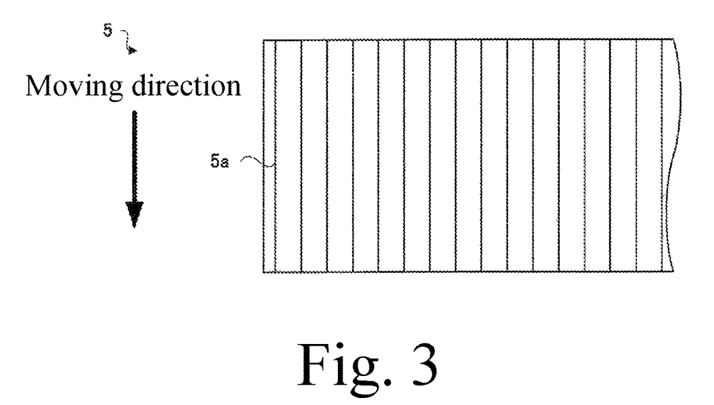
FIG. 3 is a plan view illustrating the configuration of the phase grating according to the first embodiment.

FIG. 3 illustrates the phase grating 5. The phase grating 5 has a shape such that the projection of the X-ray beam is reflected on the entire detection surface of the FPD 4. Therefore, the phase grating 5 has a rectangular shape in which the moving direction of the imaging system 3, 4, and 5 is defined as a longitudinal direction and a direction perpendicular to the moving direction is defined as a lateral direction in the same manner as in the detection surface of the FPD 4.

The phase grating 5 has a plurality of absorption lines 5a absorbing an X-ray and extending in a linear manner. The absorption line 5a is arranged at a predetermined pitch in a direction perpendicular to the extending direction. The absorption line 5a is extended in the moving direction of the imaging system 3, 4, and 5.

The main control unit 21 shown in FIG. 1 is provided for the purpose of comprehensively controlling the respective units 6, 11, 12, and 14. This main control unit 21 is configured by a CPU, and realizes each unit by executing various programs. Further, these units may be divided and executed in arithmetic units in charge of these units. Each unit can access the storage 27 as necessary. The console 25 is provided for the purpose of inputting an instruction of an operator. The display 26 is provided for the purpose of displaying the transparent image.

<X-Ray Source of Dual Energy Output Type>

According to the embodiment, the X-ray source 3 may simultaneously output X-rays different in energy. For example, the X-ray source 3 outputs a low energy X-ray (long wavelength X-ray) having an energy of 8.5 kev and a high energy X-ray (short wavelength X-ray) having an energy of 22 kev. Since the low energy X-ray and the high energy X-ray are irradiated in mutually different directions, the X-ray source 3 does not output superimposed X-rays different in energy. The difference in energy between the X-rays output from the X-ray source 3 as described above is derived from the fact that X-rays to be output differ in wavelength. The X-ray source 3 may simultaneously irradiates a high energy X-ray and a low energy X-ray.

In the phase grating 5, there exists a portion through which a low energy X-ray is transmitted and a portion through which a high energy X-ray is transmitted. These two portions do not overlap with each other. Between these two portions, the pitch of the absorption lines of the phase grating 5 can be made equal or can be made different.

<FPD Having Two Detection Surfaces>

Figure 4:
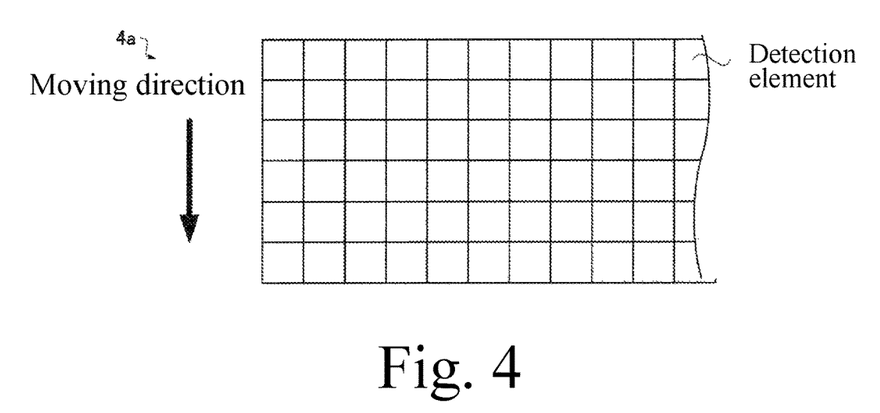
FIG. 4 is a plan view illustrating the configuration of the detection surface according to the first embodiment.

As shown in FIG. 1, the detection surface of the FPD 4 is equipped with a low energy X-ray detection surface 4a configured to detect a low energy X-ray and a high energy X-ray detection surface 4b configured to detect a high energy X-ray. FIG. 4 illustrates the low energy X-ray detection surface 4a of the FPD 4. In the low energy X-ray detection surface 4a of the FPD 4, detection elements each formed in a rectangular shape with a length of 20 μm and a width of 20 μm are arranged vertically and horizontally. The longitudinal direction of the detection element coincides with the moving direction of the imaging system 3, 4, and 5 realized by the imaging system moving mechanism 13. The low energy X-ray detection surface 4a of the FPD 4 has a rectangular shape in which the moving direction of the imaging system 3, 4, and 5 is defined as a longitudinal direction and a direction perpendicular to the moving direction is defined as a lateral direction. The low energy X-ray detection surface 4a has a width of 20 cm in the longitudinal direction and a width of 2 cm in the lateral direction. The sizes of these detection elements and detection surfaces can be changed arbitrarily.

The high energy X-ray detection surface 4b also has the same configuration as the low energy X-ray detection surface 4a described with reference to FIG. 4. Next, the positional relationship of the two detection surfaces 4a and 4b will be described. The two detection surfaces 4a and 4b are arranged in a direction in which the lateral direction coincides with the moving direction of the imaging system 3, 4, and 5. As described above, the FPD 4 of the embodiment is provided with the high energy X-ray detection surface 4b configured to detect the self-image of the phase grating 5 related to the high energy X-ray and the low energy X-ray detection surface 4a configured to detect the self-image of the phase grating 5 related to the low energy X-ray.

Figure 5:
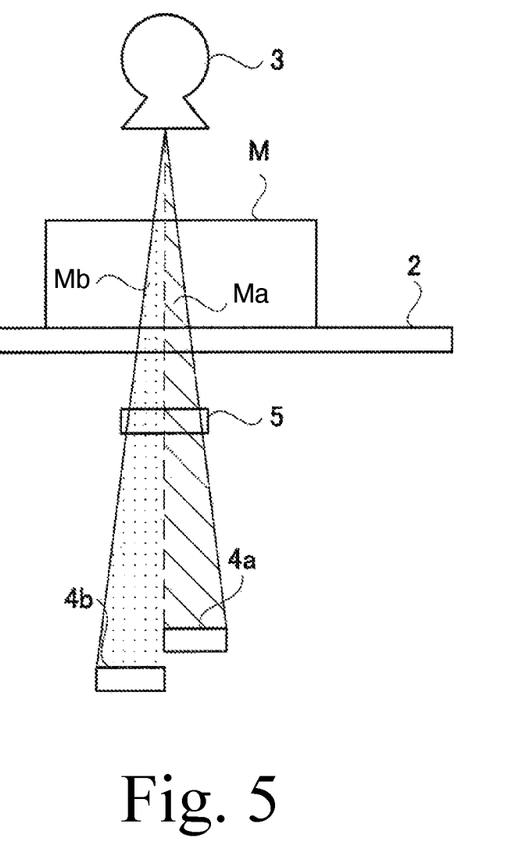
FIG. 5 is a schematic view illustrating two detection surfaces of the FPD according to the first embodiment.

As shown in FIG. 5, the X-ray irradiated by the X-ray source 3 and incident on the low energy X-ray detection surface 4a and the X-ray irradiated by the X-ray source 3 and incident on the high energy X-ray detection surface 4b are different in energy from each other. That is, the X-ray source 3 is operated such that a low energy X-ray indicated by hatching in FIG. 5 is incident on the low energy X-ray detection surface 4a and a high energy X-ray indicated by shading in FIG. 5 is incident on the high energy X-ray detection surface 4b. When X-rays are incident on respective detection surfaces 4a and 4b, the self-image of the phase grating 5 by the Talbot interference is reflected on the detection surfaces 4a and 4b.

There is a condition for the self-image of the phase grating 5 to appear on the detection surfaces 4a and 4b. That is, the distance between the detection surfaces 4a and 4b and the X-ray source 3 should be the Talbot distance. This Talbot distance varies depending on the wavelength of the X-ray. That is, there is a property that the Talbot distance becomes shorter as the wavelength of the X-ray becomes longer. Therefore, according to the configuration of the embodiment, as shown in FIG. 1, the low energy X-ray detection surface 4a is positioned closer to the phase grating 5 than the high energy X-ray detection surface 4b. In other words, the two detection surfaces 4a and 4b are separated from the phase grating 5 by the respective Talbot distances. However, since the wavelengths of X-rays directed to the two detection surfaces 4a and 4b are different from each other, the two detection surfaces 4a and 4b are arranged as shown in FIG. 1.

Therefore, the distance from the high energy X-ray detection surface 4b to the phase grating 5 of the FPD 4 is different from the distance from the low energy X-ray detection surface 4a to the phase grating 5. That is, the distance between the phase grating 5 and the low energy X-ray detection surface 4a is optimized for the low energy X-ray, and the distance between the phase grating 5 and the high energy X-ray detection surface 4b is optimized for the high energy X-ray. Therefore, the low energy X-ray generated at the X-ray source 3 transmits through the phase grating 5 and projects the self-image of the phase grating 5 on the low energy X-ray detection surface 4a. In the same manner, the high energy X-ray generated at the X-ray source 3 transmits through the phase grating 5 and projects the self-image of the phase grating 5 on the low energy X-ray detection surface 4b.

Thus, the FPD 4 of the first embodiment is composed of two detector units, a detector unit having the low energy X-ray detection surface 4a and a detector unit having the high energy X-ray detection surface 4b. The relative position of these detector units does not change during the imaging. Further, the outputs of these detector units are independent with each other.

<Self-Image Generation Unit that Generates Two Self-Images>

The output of the FPD 4 related to the low energy X-ray detection surface 4a and the output of the FPD 4 related to the high energy X-ray detection surface 4b are output to the self-image generation unit 11. The self-image generation unit 11 generates a self-image image P0a based on the output of the FPD 4 related to the low energy X-ray detection surface 4a and also generates a self-image image P0b based on the output of the FPD 4 related to the high energy X-ray detection surface 4b. The self-image of the same phase grating 5 is reflected on the respective self-image images P0a and P0b.

Now, imaging of the object M placed on the platform 2 as shown in FIG. 5 will be considered. In this case, the low energy X-ray shown by hatching in FIG. 5 and the high energy X-ray shown by shading in FIG. 5 are incident on the detection surfaces 4a and 4b through different portions of the object M, respectively. Therefore, in the state as shown in FIG. 5, imaging by the low energy X-ray can be performed only for the portion Ma of the object M through which the low energy X-ray transmits, and imaging by the high energy X-ray can be performed only for a portion Mb of the object M through which the high energy X-ray transmits.

Figure 6:
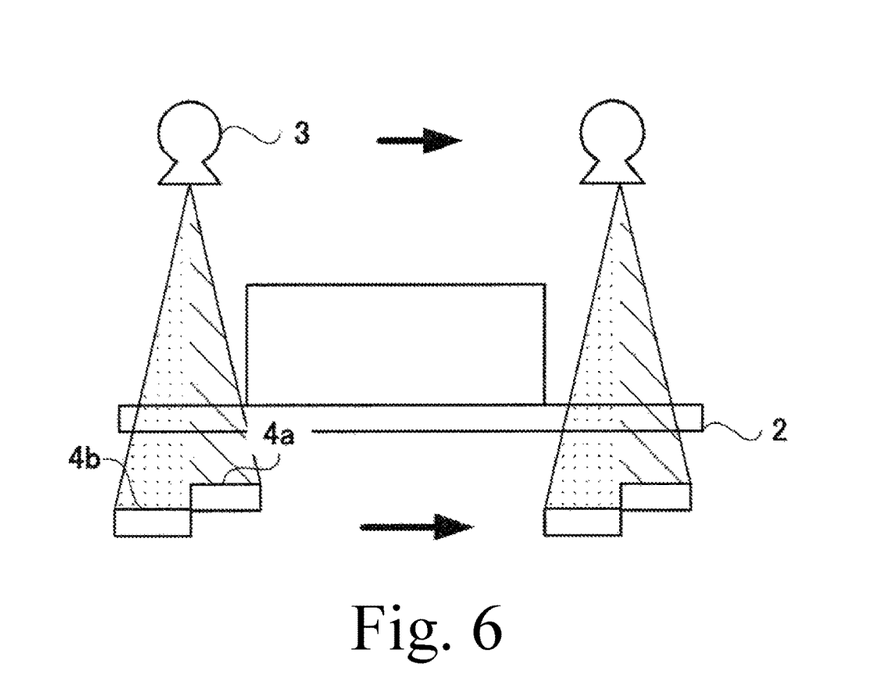
FIG. 6 is a schematic view illustrating a self-image generation unit according to the first embodiment.
Figure 7:
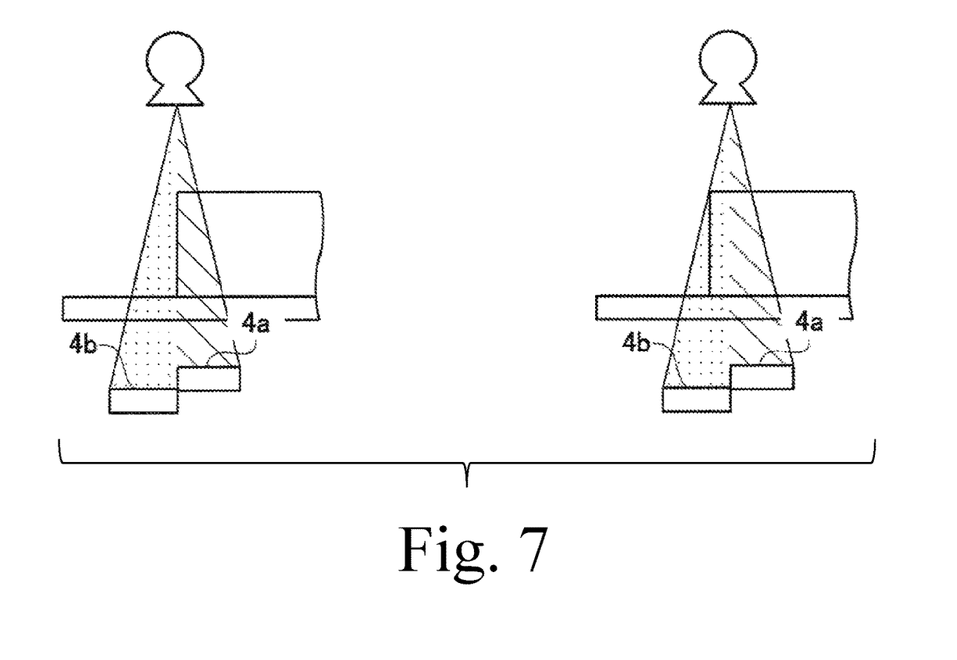
FIG. 7 is a schematic view illustrating a self-image generation unit according to the first embodiment.

Therefore, in the configuration of the embodiment, it has been devised such that imaging by the low energy X-ray and the imaging by the high energy X-ray can be performed over the entire object. The imaging by the self-image generation unit 11 may be executed by repeatedly irradiating X-rays while moving the imaging system 3, 4, and 5 with respect to the object M. FIG. 6 shows the state in which the imaging system 3, 4, and 5 is moving during the imaging operation. As the imaging system 3, 4, and 5 moves, the low energy X-ray detection surface 4a and the high energy X-ray detection surface 4b approach the object M in this order and move away from the object M in this order. FIG. 7 shows the state in which the low energy X-ray detection surface 4a and the high energy X-ray detection surface 4b pass one end of the object M. On the left side in FIG. 7, one end of the object M is imaged with the low energy X-ray detection surface 4a. On the right side in FIG. 7, the one end of the object M is imaged with the high energy X-ray detection surface 4b. As will be apparent from the above, the one end of the object M will be imaged with each of the detection surfaces 4a and 4b.

Figure 8:
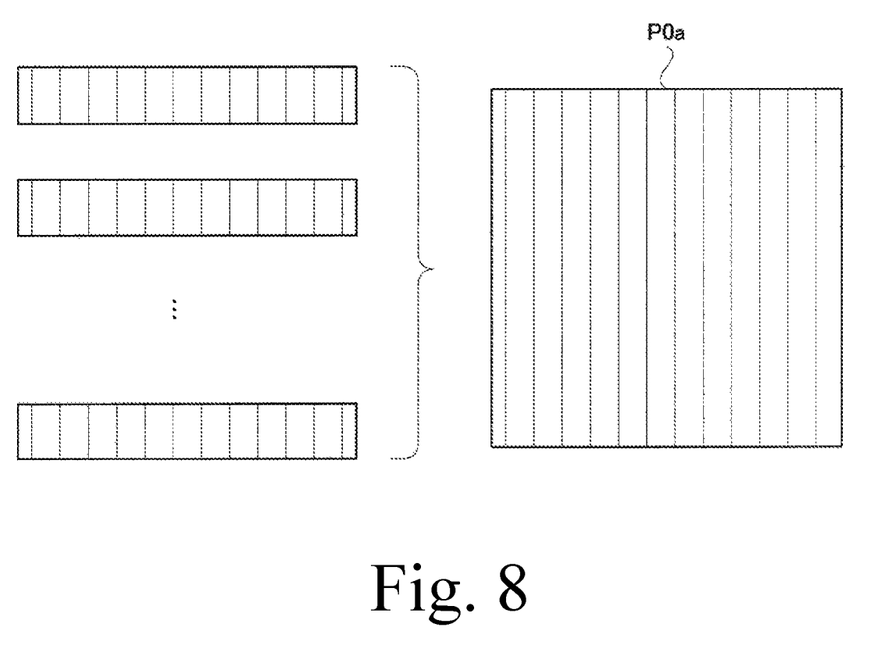
FIG. 8 is a schematic view illustrating a self-image generation unit according to the first embodiment.

The self-image generation unit 11 generates two self-image images P0a and P0b based on the detection results of the X-ray repeatedly irradiated while the imaging system 3, 4, and 5 is being moved. The self-image generation unit 11 receives from the FPD 4 the detection result of the low energy X-ray irradiated every time the X-ray is irradiated, and generates a narrow strip-like image in the moving direction of the imaging system 3, 4, and 5. As shown in FIG. 8, the self-image generation unit 11 arranges and connects a plurality of generated strip-like images in the moving direction of the imaging system 3, 4, and 5 in chronological order of imaging to generate a self-image image P0a on which the entire region of the object M is reflected. Note that the image actually reflected on the self-image image P0a is not the image of the object M itself but the self-image of the phase grating 5 disturbed by the object M.

In the same manner, the self-image generation unit 11 receives from the FPD 4 the detection result of the high energy X-ray irradiated every time the X-ray is irradiated, and generates a narrow strip-like image in the moving direction of the imaging system 3, 4, and 5. And the self-image generation unit 11 arranges and connects a plurality of generated strip-like images in the moving direction of the imaging system 3, 4, and 5 in chronological order of imaging to generate a self-image image P0b on which the entire region of the object M is reflected. The state in which the self-image image P0b is generated at this time is the same as shown in FIG. 8. Note that the image actually reflected on the self-image image P0b is not the image of the object M itself but the self-image of the phase grating 5 disturbed by the object M.

In this manner, the self-image generation unit 11 generates the self-image image P0a for the entire region of the object based on the detection result of the low energy X-ray detection surface 4a and also generates the self-image image P0b for the entire region of the object based on the detection result of the high energy X-ray detection surface 4b. The self-image image P0a represents the disturbance of the self-image of the phase grating observed when a low energy X-ray is irradiated to the object M, and the self-image image P0b represents the disturbance of the self-image of the phase grating when a high energy X-ray is irradiated to the object M. In this way, the self-image generation unit 11 takes the self-image from the detection result of the X-ray by the high energy X-ray detection surface 4b of the FPD 4, and takes the self-image from the detection result of the X-ray by the low energy X-ray detection surface 4a of the FPD 4.

<Transparent Imaging Generation Unit for Generating Two Transparent Images>

The self-image generation unit 11 sends the self-image images P0a and P0b to the transparent image generation unit 12. The transparent image generation unit 12 generates a transparent image P1a on which the transparent image of the object M is reflected on the basis of the self-image image P0a and also generates the transparent image P1b on which the transparent image of the object M is reflected on the basis of the self-image image P0b. In this way, the transparent image generation unit 12 generates a transparent image of the object M from the self-image related to the high energy X-ray imaged by the self-image generation unit 11, and also generates the transparent image of the object M from the self-image related to the low energy X-ray imaged by the self-image generation unit 11. The generated transparent images P1a and P1b are arranged side by side and displayed on the display 26.

Figure 9:
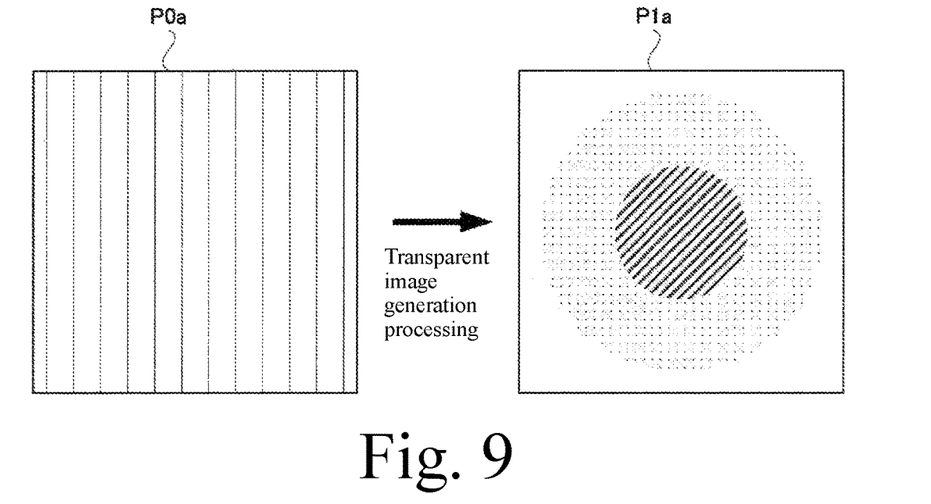
FIG. 9 is a schematic view illustrating the transparent image according to the first embodiment.
Figure 10:
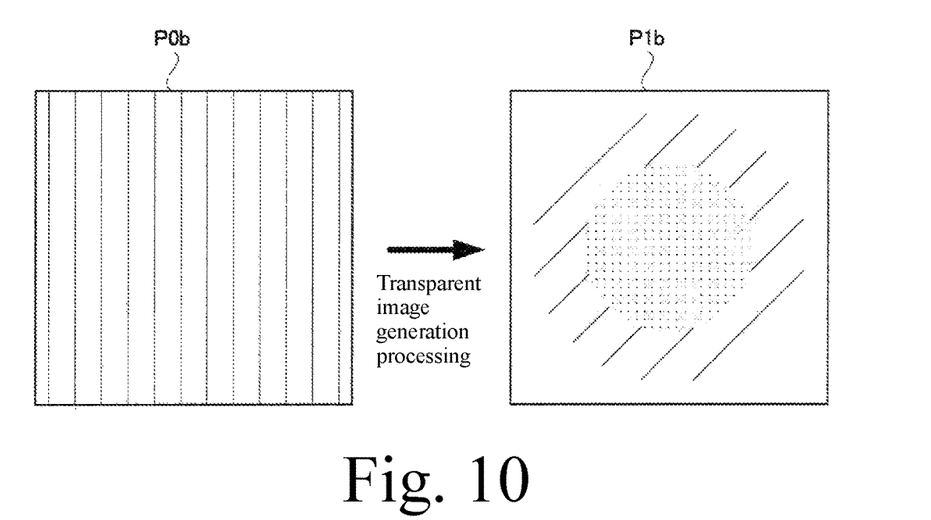
FIG. 10 is a schematic view illustrating the transparent image according to the first embodiment.

FIGS. 9 and 10 schematically illustrate transparent images P1a and P1b obtained when a spherical object M is imaged. Such an object M has a property that the peripheral portion is likely to transmit an X-ray therethrough and the central portion is likely to absorb the X-ray.

FIG. 9 shows how the transparent image P1a is generated. The transparent image P1a is a result of imaging the object M with a low energy X-ray. In the transparent image P1a, the state of the inside of the peripheral portion of the object M is clearly reflected. A low energy X-ray is suitable for imaging a part of an object through which an X-ray readily transmits. However, the center portion of the object M reflected on the transparent image P1a is not always clear. This is because in some case a low energy X-ray cannot transmit through the center portion of an object M. The apparatus of the embodiment is configured to visualize how much the phase of the X-ray that transmitted through the object M has changed. Therefore, unless an X-ray can sufficiently transmit through an object M, the inside of the object cannot be sharply imaged.

FIG. 10 shows how the transparent image P1$b$ is generated. The transparent image P1$b$ is a result of imaging the object M with a high energy X-ray. In the transparent image P1$b$, at the center portion of the object M, the state of the inside of the object M is clearly reflected. A high energy X-ray is suitable for imaging a part of an object through which an X-ray hardly transmits. However, the peripheral portion of the object M reflected on the transparent image P1$b$ is not always clear. This is because the high energy X-ray transmitted through the peripheral portion of the object M. The apparatus of the embodiment is configured to visualize how much the phase of the X-ray that transmitted through the object M has changed. Therefore, unless the phase of X-ray that passed through the object M has changed sufficiently, sharp imaging of the inside of the object cannot be performed.

According to the apparatus of the embodiment, by comparing the two transparent images P1$a$ and P1$b$ having different imaging conditions, the state of the inside of the object M can be accurately known. That is, when it is desired to grasp the internal structure of the peripheral portion of the object M, the internal structure can be grasped by referring to the transparent image P1$a$, and when it is desired to grasp the internal structure of the center portion of the object M, the internal structure can be grasped by referring to the transparent image P1$b$.

As described above, according to the embodiment, it is possible to provide a radiation phase-contrast imaging device capable of easily performing imaging of an object using X-rays of a plurality of energies. That is, the configuration of the embodiment includes an X-ray source 3 of a dual energy output type, and an FPD 4 having a high energy X-ray detection surface 4$b$ and a low energy X-ray detection surface 4$a$ so that two types of imaging, imaging by high energy X-ray and imaging by low energy X-ray, can be performed. By imaging so as to scan the object M while changing the relative position of the imaging system and the object M, two types of imaging can be completed at once.

The present invention can also be applied to a transparent image using small-angle scattering, and therefore small-angle scattering will be briefly described first. When applying an X-ray to an object, there occurs a phenomenon in which the traveling direction of some X-rays changes in the object. Such a phenomenon is called X-ray scattering. Among the X-ray scattering, scattering in which the traveling direction hardly changes is called small-angle scattering. Such X-ray related to small-angle scattering is detected by the FPD 4 and reflected on the self-image images P0$a$ and P0$b$ generated by the self-image generation unit 11. The transparent image generation unit 12 can extract a component related to the small-angle scattering from each of the self-image images P0$a$ and P0$b$ to generate a small-angle scattering image. There are two small-angle scattering images generated at this time, one generated based on the self-image image P0$a$ and the other generated based on the self-image image P0$b$.

When considering the phenomenon of small-angle scattering, it is easy to understand if the structure constituting the inside of the object is considered as particles. It is considered such that small-angle scattering will occur when an X-ray hits the particles. Small-angle scattering X-ray generated by irradiating a low energy X-ray to an object is derived from particles having a relatively large diameter among the particles constituting the inside of the object. On the other hand, small-angle scattering X-ray generated by irradiating a high energy X-ray to an object is derived from particles having a relatively small diameter among the particles constituting the inside of the object. Thus, when changing the wavelength of the X-ray used for imaging a small-angle scattering image, the image reflected on the small-angle scattering image changes. The small-angle scattering image took by irradiating a low energy X-ray to the object is one in which large diameter particles constituting the inside of the object are reflected. On the other hand, the small-angle scattering image took by irradiating a high energy X-ray to the object is one in which small diameter particles constituting the inside of the object are reflected.

According to the configuration of the embodiment, it is possible to simultaneously perform imaging using a low energy X-ray and imaging using a high energy X-ray, so two small-angle scattering images can be acquired at the same time. That is, from the self-image image P0$a$ related to a low energy X-ray, a small-angle scattering image in which particles of a large diameter constituting the inside of the object are reflected can be generated. On the other hand, from the self-image image P0$a$ related to a high energy X-ray, a small-angle scattering image in which particles of a small diameter constituting the inside of the object are reflected can be generated.

The present invention is not limited to the aforementioned configurations, and may be modified as follows.

(1) According to the aforementioned embodiment, the imaging system moving mechanism 13 is configured to move the X-ray source 3 together with the FPD 4 and the phase grating 5, but the present invention is not limited thereto. It may be configured such that the relative positions of the object M and the imaging system are changed by configuring the imaging system moving mechanism 13 so as to move the FPD 4 and the phase grating 5 by tracing the locus of the circular arc so as not to change the positional relationship of the X-ray source 3, the FPD 4 and the phase grating 5. Further, it may be configured such that the relative position of the object M and the imaging system is changed by moving the platform 2 without moving the imaging system 3, 4, and 5.

(2) According to the aforementioned configuration, although the object M is placed between the X-ray source 3 and the phase grating 5, the present invention is not limited to the configuration. The platform 2 and the object M may be placed between the phase grating 5 and the FPD 4.

(3) According to the aforementioned embodiment, the X-ray source 3 simultaneously irradiates a low energy X-ray and a high energy X-ray, but the present invention is not limited to this configuration. It may be configured such that the X-ray source 3 alternately irradiates a low energy X-ray and a high energy X-ray.

(4) According to the aforementioned embodiment, although the low energy X-ray detection surface 4$a$ and the high energy X-ray detection surface 4$b$ include detection elements arranged with the same pitch, the present invention is not limited to this configuration. It may be configured such that the pitch of the detection elements is changed between the detection surface 4$a$ and the detection surface 4$b$.

(5) According to the aforementioned configuration, although it is configured such that the low energy X-ray and the high energy X-ray transmit through the same phase grating 5, the present invention is not limited to the configuration. It may be configured such that a low energy X-ray phase grating 5 through which a low energy X-ray transmits and a high energy X-ray phase grating 5 through which a high energy X-ray transmits are provided and the pitch of absorption lines constituting the low energy X-ray phase grating 5 and the pitch of the absorption lines constituting the high energy X-ray phase grating 5 are different from each other.

(6) In the configuration in which phase gratings 5 having different absorption line pitches are provided, the Talbot distance related to the low energy X-ray and the Talbot distance related to the high energy X-ray may be set so as to coincide with each other. In this case, the distance from the low energy X-ray detection surface 4a to the phase grating 5 is different from the distance from the high energy X-ray detection surface 4b to the phase grating 5 coincide.

(7) According to the above-described embodiment, the FPD 4 is configured to directly observe the self-image, but the present invention is not limited to this configuration. It may be configured such that an absorption grating is arranged so as to cover the detection surfaces 4a and 4b and the moire generated between the self-image and the absorption grating is observed with the detection surfaces 4a and 4b.

(8) The above-described X-ray source 3 is a dual energy output type, but the present invention is not limited to this configuration. In place of this, the X-ray source 3 of the present invention may be configured to output a wideband X-ray. Since such an X-ray source 3 outputs X-rays of various wavelengths, monochromatic X-ray is not incident on a low energy radiation detection surface 4a and a high energy radiation detection surface 4b. However, the wavelength of X-ray that can be involved in generating the self-image depends on the distance from the phase grating 5 to the detection surfaces 4a and 4b. Therefore, also in the present invention, it is a low energy X-ray having a certain wavelength that reflects the self-image on the low energy radiation detection surface 4a, and it is a high energy X-ray having a certain wavelength that reflects the self-image on the low energy radiation detection surface 4b. In this manner, the transparent images P1a and P1b described with reference to FIGS. 9 and 10 can be acquired without using the dual energy output type X-ray source 3. An X-ray self-image of which wavelength appears on the detection surfaces 4a and 4b is determined not only by the distance between the phase grating 5 and the detection surfaces 4a and 4b but also by the pitch of the absorption lines 5a arranged in the phase grating 5 as well. Therefore, the wavelength of the X-ray for generating the self-image can be selected by appropriately changing the distance between the phase grating 5 and the detection surfaces 4a and 4b and the pitch of the absorption lines 5a of the phase grating 5.

DESCRIPTION OF REFERENCE SYMBOLS

3: X-ray source (radiation source)
4: FPD (detection unit)
4a: low energy radiation detection surface
4b: high energy radiation detection surface
5: phase grating (grating)
11: self-image generation unit (self-image generation unit)
12: transparent image generation unit (transparent image generation unit)
13: imaging system moving mechanism (position changing unit)

The invention claimed is:

1. A radiation phase-contrast imaging device comprising:
a radiation source configured to irradiate high energy radiation and low energy radiation;
a grating in which an absorber absorbing radiation and extending in one direction is arranged in a direction perpendicular to the one direction, the absorber generating Talbot interference when the radiation transmits therethrough;
a detection unit including a high energy radiation detection surface configured to detect a self-image of the grating related to the high energy radiation and a low energy radiation detection surface configured to detect a self-image of the grating related to the low energy radiation; and
a position changing unit configured to change a relative position of an imaging system and an object so that a projection of the object moves on the detection surface while keeping a positional relationship of the radiation source, the grating, and the detection unit, the imaging system being configured by the radiation source, the grating, and the detection unit.

2. The radiation phase-contrast imaging device as recited in claim 1,
wherein a distance from the high energy radiation detection surface of the detection unit to the grating and a distance from the low energy radiation detection surface to the grating are different from each other.

3. The radiation phase-contrast imaging device as recited in claim 1,
wherein the position changing unit moves the detection unit in a state in which a positional relationship between the high energy radiation detection surface and the low energy radiation detection surface is maintained.

4. The radiation phase-contrast imaging device as recited in claim 1, further comprising a self-image generation unit configured to image a self-image from a detection result that the detection unit detects the radiation at the high energy radiation detection surface and a self-image from a detection result that the detection unit detects the radiation at the low energy radiation detection surface.

5. The radiation phase-contrast imaging device as recited in claim 4, further comprising a transparent image generation unit configured to generate a transparent image of the object from the self-image related to the high energy radiation and imaged by the self-image generation unit and a transparent image of the object from the self-image related to the low energy radiation and imaged by the self-image generation unit.

6. The radiation phase-contrast imaging device as recited in claim 1, wherein the radiation source is configured to simultaneously irradiate the high energy radiation and the low energy radiation onto the grating.

7. The radiation phase-contrast imaging device as recited in claim 1,
wherein a first portion of the grating is positioned to receive the low energy radiation and a second portion of the grating is positioned to receive the high energy radiation, and
the absorption lines of the first portion of the grating and the absorption lines of the second portion of the grating have the same pitch.

8. The radiation phase-contrast imaging device as recited in claim 1,
wherein the detection unit is configured to have the low energy radiation detection surface spaced apart from a platform interposed between the radiation source and the detection unit by a first distance and the high energy radiation detection surface spaced apart from the platform by a second distance different from the first distance.

9. The radiation phase-contrast imaging device as recited in claim 8, wherein the low energy radiation detection surface and the high energy radiation detection surface each comprise a plurality of detection elements.

10. The radiation phase-contrast imaging device as recited in claim 8, wherein a first distance between the grating and the high energy radiation detection surface is different than a second distance between the grating and the low energy radiation detection surface.

11. The radiation phase-contrast imaging device as recited in claim 1, wherein the low energy radiation detection surface includes a plurality of detection elements, each detection element being formed in a rectangular shape.

12. The radiation phase-contrast imaging device as recited in claim 11, wherein the high energy radiation detection surface has a similar configuration as the low energy X-ray detection surface.

13. The radiation phase-contrast imaging device as recited in claim 1, wherein the position changing unit is further configured to change the relative position of the imaging system and a platform by linearly relatively moving the imaging system in a direction parallel to the platform.

14. The radiation phase-contrast imaging device as recited in claim 1, further comprising a self-image generation unit that is configured to generate a first self-image from a first plurality of narrow strip-like images obtained from the high energy radiation detection surface and a second self-image related to the low energy radiation from a second plurality of narrow strip-like images obtained from the low energy radiation detection surface.

15. The radiation phase-contrast imaging device as recited in claim 14, further comprising a transparent image generation unit that is configured to generate a first transparent image on the basis of the first self-image and a second transparent image on the basis of the second self-image.

16. The radiation phase-contrast imaging device as recited in claim 15, further comprising a display configured to simultaneously display the first transparent image and the second transparent image side by side.

17. A radiation phase-contrast imaging device comprising:
a radiation source configured to irradiate high energy radiation and low energy radiation;
at least one phase grating comprising a plurality of absorption lines extending in a first direction and configured to absorb the high energy radiation and the low energy radiation at a first plane and generate Talbot interference in response to the high energy radiation and the low energy radiation transmitting therethrough;
a detection unit including a first radiation detection surface configured to detect a first self-image of the phase grating related to the high energy radiation and a second radiation detection surface configured to detect a second self-image of the phase grating related to the low energy radiation; and
a position changing unit configured to change a relative position of a platform with respect to the radiation source, the phase grating, and the detection unit.

18. The radiation phase-contrast imaging device as recited in claim 17, wherein the position changing unit is further configured to change the relative position by linearly moving the platform or linearly moving the radiation source, the phase grating, and the detection together.

19. The radiation phase-contrast imaging device as recited in claim 18,
wherein the at least one phase grating comprises a first phase grating positioned to receive the low energy radiation and a second phase grating positioned to receive the high energy radiation, and
wherein the first phase grating comprises first absorption lines spaced apart at a first pitch and the second phase grating comprises second absorption lines spaced apart at a second pitch different from the first pitch.

20. The radiation phase-contrast imaging device as recited in claim 17, wherein the first radiation detection surface has a similar configuration as the second radiation detection surface.

* * * * *